(12) United States Patent
Rem-Bronneberg et al.

(10) Patent No.: US 11,185,720 B2
(45) Date of Patent: Nov. 30, 2021

(54) ULTRASOUND PATCH FOR ULTRASOUND HYPERTHERMIA AND IMAGING

(71) Applicant: KONINKLIJKE PHILIPS N.V., Eindhoven (NL)

(72) Inventors: Debbie Rem-Bronneberg, Eindhoven (NL); Aaldert Jan Elevelt, Eindhoven (NL); Sergei Shulepov, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 339 days.

(21) Appl. No.: 15/517,546

(22) PCT Filed: Oct. 12, 2015

(86) PCT No.: PCT/EP2015/073494
§ 371 (c)(1),
(2) Date: Apr. 7, 2017

(87) PCT Pub. No.: WO2016/058963
PCT Pub. Date: Apr. 21, 2016

(65) Prior Publication Data
US 2018/0264291 A1    Sep. 20, 2018

(30) Foreign Application Priority Data

Oct. 17, 2014    (EP) ..................................... 14189299

(51) Int. Cl.
*A61B 8/00* (2006.01)
*A61N 7/02* (2006.01)
(Continued)

(52) U.S. Cl.
CPC .............. *A61N 7/02* (2013.01); *A61B 8/4488* (2013.01); *A61B 2018/00023* (2013.01);
(Continued)

(58) Field of Classification Search
CPC .................... A61N 7/02; A61B 8/4488; A61B 2018/00005
See application file for complete search history.

(56) References Cited

U.S. PATENT DOCUMENTS 7,850,626 B2 * 12/2010 Vaezy ...................... A61B 8/08
600/101
2005/0251044 A1   11/2005 Hoctor et al.
(Continued)

FOREIGN PATENT DOCUMENTS

CN          102164542 A     8/2011
WO       2008137030 A1    11/2008

*Primary Examiner* — Jonathan Cwern
*Assistant Examiner* — Amal Aly Farag

(57) ABSTRACT

An ultrasound system for an ultrasound therapy (ablation or hyperthermia) of a region of interest comprising: a patch comprising a two-dimensional array of ultrasonic transducers (preferably CMUTs) arranged on a support, wherein a plurality of the transducers is adapted to operate in a variable frequency range; a transducer controller means adopted to activate at least two groups of the plurality of the transducers in the array for a transmission of the ultrasound signals, wherein each of the at least two groups: is arranged in a pattern; and operates at a frequency different from other group's frequency.

18 Claims, 7 Drawing Sheets

(51) Int. Cl.
*A61N 7/00* (2006.01)
*A61B 18/00* (2006.01)

(52) U.S. Cl.
CPC ........... *A61N 2007/0073* (2013.01); *A61N 2007/0078* (2013.01); *A61N 2007/0095* (2013.01)

(56) References Cited

U.S. PATENT DOCUMENTS

| | | | | |
|---|---|---|---|---|
| 2006/0058707 | A1* | 3/2006 | Barthe | A61N 7/022 601/2 |
| 2007/0049827 | A1* | 3/2007 | Donaldson | A61B 5/0215 600/443 |
| 2007/0066897 | A1 | 3/2007 | Sekins et al. | |
| 2007/0260144 | A1* | 11/2007 | Sela | B01D 19/0084 600/472 |
| 2008/0004614 | A1* | 1/2008 | Burdette | A61N 7/02 606/27 |
| 2008/0045882 | A1 | 2/2008 | Finsterwad | |
| 2008/0051656 | A1* | 2/2008 | Vaezy | A61B 8/08 600/439 |
| 2008/0139943 | A1* | 6/2008 | Deng | A61M 37/0092 600/459 |
| 2008/0304729 | A1* | 12/2008 | Peszynski | A61B 8/4236 382/131 |
| 2009/0082673 | A1* | 3/2009 | Lu | A61B 8/4281 600/459 |
| 2009/0088623 | A1 | 4/2009 | Vortman et al. | |
| 2010/0152587 | A1* | 6/2010 | Haider | A61B 8/00 600/459 |
| 2011/0095645 | A1* | 4/2011 | Chang | B06B 1/0292 310/300 |
| 2011/0118600 | A1 | 5/2011 | Gertner | |
| 2011/0213248 | A1 | 9/2011 | Murakami et al. | |
| 2012/0010538 | A1* | 1/2012 | Dirksen | A61B 8/00 601/2 |
| 2012/0253176 | A1* | 10/2012 | Dumoulin | A61N 7/02 600/411 |
| 2012/0277639 | A1 | 11/2012 | Pollock et al. | |
| 2013/0079621 | A1* | 3/2013 | Shoham | A61M 37/0092 600/407 |
| 2013/0178915 | A1* | 7/2013 | Radziemski | A61M 1/127 607/61 |
| 2014/0005521 | A1* | 1/2014 | Kohler | A61B 5/4836 600/411 |
| 2014/0257262 | A1 | 9/2014 | Carpentier et al. | |
| 2014/0288428 | A1 | 9/2014 | Rothberg et al. | |
| 2015/0065922 | A1 | 3/2015 | Kohler | |
| 2015/0258353 | A1* | 9/2015 | Partanen | A61B 5/055 600/411 |
| 2016/0199030 | A1* | 7/2016 | Patil | B06B 1/02 600/459 |
| 2017/0007853 | A1* | 1/2017 | Alford | A61B 5/4848 |

\* cited by examiner

ULTRASOUND PATCH FOR ULTRASOUND HYPERTHERMIA AND IMAGING

This application is the U.S. National Phase application under 35 U.S.C. § 371 of International Application No. PCT/EP2015/073494, filed on Oct. 12, 2015, which claims the benefit of EP Application Serial No. 14189299.2, filed Oct. 17, 2014. These applications are hereby incorporated by reference herein.

FIELD OF THE INVENTION

The invention relates to an ultrasound system for an ultrasound hyperthermia or ablation therapy of a region of interest comprising a patch comprising a two-dimensional array of ultrasonic transducers (CMUTs) arranged on a support. The invention further relates to a method of a ultrasound therapy.

BACKGROUND OF THE INVENTION

According to the National Cancer Institute (NCI), it is believed that heat may help shrink tumors by damaging cells or depriving them of the substances they need to live and make the tumor cells more susceptible to adjuvant therapies (such as radiation or chemo therapy). There are many techniques by which heat may be delivered. Some of the most common involve the use of ultrasound, radiofrequency, microwave, infusion of warmed liquids, or direct application of heat such as through sitting in a hot room or wrapping a patient in hot blankets. The hyperthermia treatment depth and volume depends on the physical characteristics of the energy source and the type of device that was used. Members of the European Society of Hyperthermia Oncology (ESHO) defined an extensive guideline for mild regional hyperthermia as part of an overall quality assurance (QA) program in mild hyperthermia (Langendijk et al 1998). In terms of this guideline, each hyperthermia treatment system should be able to maintain temperatures in the target volume between 40 and 43° C. for at least 60 min. At temperatures of around 40-45° C., irreversible cell damage occurs only after prolonged exposure (from 30 to 60 minutes). At temperatures of above 60° C., the time that is required to achieve irreversible damage decreases exponentially. Inactivation of vital enzymes is an initial feature of injury. Above 60° C., rapid protein denaturation occurs, which is immediately cytotoxic and leads to coagulative necrosis.

Ultrasound therapy can be used as hyperthermia technique as well as an ablation therapy to kill tissue by coagulation. The RF ablation technique is widely used for tumor ablation, but this technique always requires insertion of the RF ablation probe while with ultrasound therapy energy (causing temperature increase) can be delivered from a distance. However, external hyperthermia systems for local superficial hyperthermia therapy, such as microwave, radio frequency or heating pads, are limited in applying selective and controlled tissue heating. The planned target volume and/or depth can either not be reached with the current devices or the temperature in the target volume cannot be maintained without affecting the surrounding healthy tissue. Different ultrasound intensities (W/cm$^2$) are needed to reach either mild hyperthermia (at temperatures around 40-43° C.) or thermal ablation (at temperatures above 52-60° C.). An ultrasound transducer patch comprising flexible stripes of printed circuit boards and an array of piezoelectric transducers (PZTs) mounted thereon is known from US2012/0277639 A1. The ultrasound patch known from the prior art document is a thin and flexible patch developed for an ultrasound dermal therapy application. The PZTs of the patch are dual frequency transducers of either "unimorph" or "bimorph" structure, manufactured to operate in one of the two frequencies: 50 kHz or 3 MHz.

The disadvantage of the patch known from US2012/0277639 A1 is that the dual-frequency PZT transducers in the patch are small compared to the wavelength of the low frequency ultrasound component. The prior art recognizes that the small size of the PZT based transducers limits the depth of the ultrasound wave propagation due to the divergent beam profile. As an attempt to solve this problem, a clustering of the transducers in the clusters, sizes of which are comparable to a size of the ultrasound wave wavelength is suggested. However, this solution creates a complicated depth propagation profile for the ultrasound wave, wherein the amplitude of the propagating into the body ultrasound wave changes non-homogenously.

Another disadvantage of such a patch is its limitation to only two-operational frequencies due to a narrow band frequency range of the piezoelectric based ultrasound transducers.

In hyperthermia and ablation therapy, wherein a high intensity ultrasound is used, the exact temperature distribution in the tissue during the treatment is very important.

SUMMARY OF THE INVENTION

It is an object of the present invention to provide an ultrasound system, which enables a more accurate temperature distribution in the tissue during treatment.

This object is achieved according to the invention by an ultrasound system for an ultrasound therapy of a region of interest comprising: a patch comprising a two-dimensional array of capacitive micromachined ultrasound transducers (CMUTs) arranged on a support, wherein a plurality of the transducers is adapted to operate in a variable frequency range; transducer controller means adopted to activate at least two groups of the plurality of the transducers in the array for a transmission of the ultrasound signals into the region of interest, wherein each of the at least two groups is arranged in a pattern; and operates at a frequency different from other group's frequency, wherein the frequency of each group decreases with an average distance between the group and the region of interest.

In accordance with the present invention providing transducer controller means permits continuously varying the frequencies, at which the transducers in the array can be operated. The transducer controller means may activate the transducers operating at different frequencies either simultaneously or in a predefined sequence. The attenuation length of the ultrasound wave in the body decreases with increased frequency, thus, activating transducers in the groups of different patterns and increasing the frequency of the activated group with an increasing average distance from the group to the region of interest gives a control over the penetration depth of the transmitted ultrasound wave. The capacitive micromachined ultrasound transducers including an integrated circuitry coupled to the transducers can be manufactured in a single flow of the semiconductor processing steps. This permits producing a compact ultrasound patch applicable for hyperthermia or ablation treatment. Another advantage of the CMUTs is a wide band frequency range, in which the single transducer can be operated.

In an embodiment of the invention the patterns of the transducers groups form concentric shapes, wherein a group having an innermost pattern is adapted to operate at a first frequency being a maximum frequency of the activated groups and a group having an outermost pattern is adapted to operate at a second frequency being smaller than the first frequency, said second frequency is a minimum frequency of the activated groups.

The formation of the group's pattern operating at different frequencies in the concentric circles provides an opportunity of more homogenous exposure of the region of interest with the high intensity ultrasound. A gradual reduction of frequency of the activated groups forming the concentric shaped patterns allows compensating for the frequency dependent acoustic wave attenuation. The inner most pattern can be formed by the group activated to have the closest average distance to the region of interest and to operate at a maximum frequency in a selected frequency range. The outmost pattern can be formed by the group activated to have the farthest average distance to the region of interest and to operate at a minimum frequency in the selected frequency range. Due to the decrease in the attenuation length of the ultrasound wave in the body with increased wave frequency, this embodiment provides an improved homogeneity in acoustic wave intensity transmitted to the region of interest. In addition, this embodiment also improves focusing of the ultrasound beam.

In another embodiment of the invention, the variable frequency range expands from 500 kHz up to 10 MHz.

The low frequency range (kHz) can be used to in hyperthermia treatment of the large areas, while higher frequency range used to target the localized areas.

In a further embodiment of the invention, the operational frequency of the group decreases with an increase of the average distance between the group and the region of interest.

This embodiment provides an additional improvement of the homogenous exposure of the region of interest, wherein the correction on the acoustic wavelength dependent attenuation is performed. The region of interest is located in a tissue having its own dispersion coefficient. In most tissues the attenuation length of the propagating acoustic wave decreases with increasing frequency. Thus, in order to assure the delivery of the ultrasound wave to the region of interest the frequency of operation of each group in the array would decrease with an increase of the average distance between the group and the region of interest.

In yet another embodiment the transducer controller means adopted to activate at least one of the at least two groups of the transducers transmitting the ultrasound signals with different intensity from the signal intensity of other groups.

Changing the intensity of the selected groups in the array gives an additional control over the delivered ultrasound to the region of interest, thus, permitting to have a controllable temperature profile in the region of interest.

In a further embodiment the ultrasound signals simultaneously transmitted by the groups have variable intensity in in one of the ranges of 4 to 10 W/cm$^2$, 4 to 50 W/cm$^2$, 100 mW/cm$^2$ to 4 W/cm$^2$ and 100 m W/cm$^2$ to 52 W/cm$^2$.

This intensity range covers the ultrasound therapy application area: from hyperthermia, requiring low intensity, to ablation, requiring higher intensity treatments.

In yet another embodiment of the invention, the system further comprises: tracking means adapted to register the patch into a registered medical image of the region of interest; and a pattern processor, adapted to process the registered medical image and coupled to the transducer controller means, wherein the pattern processor is further adapted to define the pattern of each group in the array based on a location and dimensions of the region of interest in the registered medical image.

This embodiment describes a patient's targeted therapy, wherein the pattern of each group operating at the same frequency can be predefined based on the actual dimensions and location of the region of interest extracted from the medical image obtained by one of the common medical imaging systems, such as MRI, X-ray or ultrasound. The tracking means register the patch's location into the medical image of the region and provide a registered medical image. The pattern of each group is determined by the pattern processor, which processes the registered image, and is defined by the depth at which the region of interest is located, its dimensions and size.

In a further embodiment of the invention, the intensity of the ultrasound signals simultaneously transmitted by the same group is predefined by an average distance between the group and the region of interest.

The transducer controller means permit changing the intensity of the transmitted signal by the same group in dependence with the average distance between this group and the region of interest. This is a possibility of redistributing the increased temperature in the region of interest and reducing a high intensity exposure of the tissue located beyond the region of interest.

In another embodiment of the present invention the patch further comprises an integrated circuitry which is coupled to the CMUTs and adapted to provide at least partial beamforming of the ultrasound signals.

The advantage of the CMUTs application as ultrasound transducers is a possibility of combining both functionalities: ultrasound treatment and imaging capabilities using ultrasound. The semiconductor processing allows a manufacturing of the CMUTs together with a coupled to the CMUTs integrated circuitry in one workflow. The integrated circuitry can be also adapted to perform at least partial focusing and/or beamforming of the ultrasound signal, which can be further used in the reconstruction of an ultrasound image of the treated region of interest.

These and other aspects of the invention will be apparent from and elucidated with reference to the embodiments described hereinafter.

DETAILED DESCRIPTION OF EMBODIMENTS

Figure 1A:
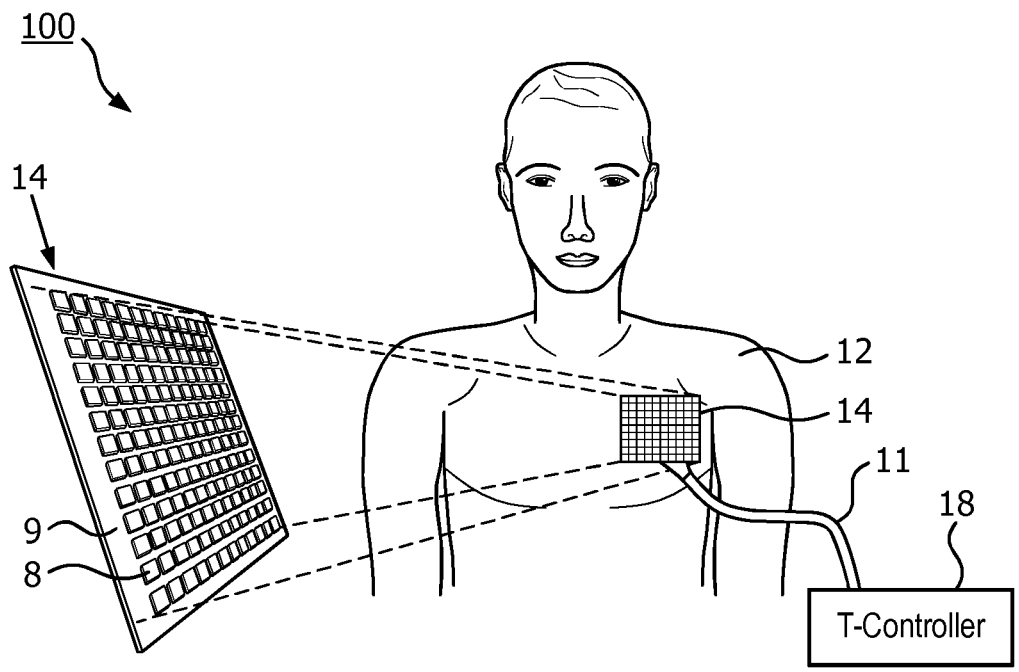
FIG. 1a illustrates an ultrasound system for an ultrasound therapy of a region of interest operated in accordance with the principles of the present invention.

FIG. 1a shows schematically and exemplarily an ultrasound system 100 for an ultrasound therapy treatment of a region of interest 12. The ultrasound system comprises a patch 14 comprising a two-dimensional (2D) array of ultrasonic transducers 8 arranged on a support 9. Each of the ultrasound transducers in the array is adapted to operate in a range of variable ultrasound frequencies that may be used in HIFU treatment. The transducers in the 2D array can be activated in groups of different patterns via the transducer controller 18. The operational frequency of the transducers comprising the same group is kept the same within the group and differs from the operational frequency of other groups. In most tissues, being exposed during the ultrasound hyperthermia treatment, the attenuation coefficient of ultrasound wave increases with increasing frequency of the ultrasound wave. Thus, a propagation depth into a region of interest for the ultrasound waves with relatively higher frequencies is lower compared to the depth of the waves with relatively lower frequencies. The present invention provides the patch 14 and the transducer controller 18 that can simultaneously activate transducers 8 at different frequencies thus simultaneously addressing the region of interest at different depths with the ultrasound treatment.

Figure 1B:
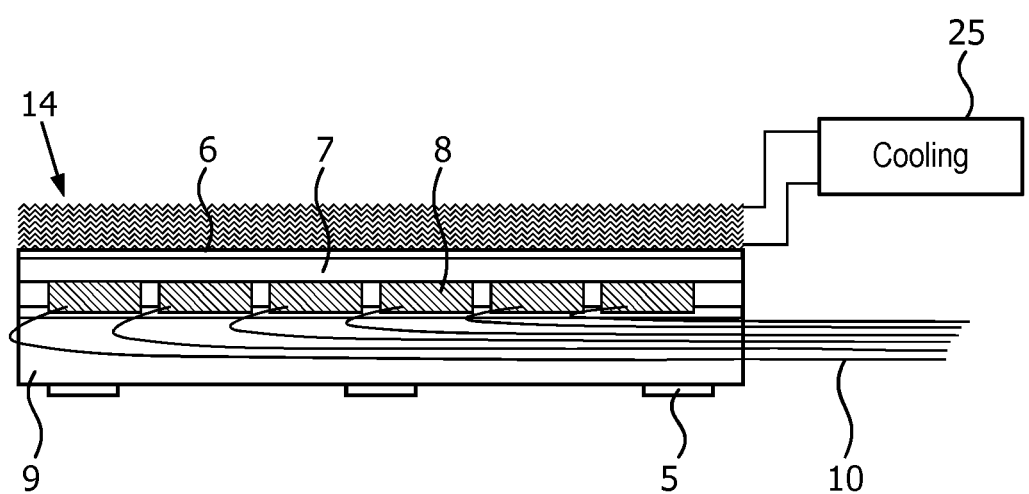
FIG. 1b illustrates a patch comprising a two-dimensional array of ultrasonic transducers arranged on a support.

FIG. 1b illustrates in more detail an embodiment of the patch 14 in accordance with present invention. The 2D transducer array comprises ultrasound transducers 8 arranged on the front side of the support 9. The ultrasound transducers may be represented by the capacitive micromachined transducers (CMUTs). As described below, CMUT provides an exclusive possibility of transmitting the ultrasound wave in a broad range of frequencies with a single transducer. The transmitting surface of the transducers may be overlaid with an acoustic window 7 followed by an optional additional layer of an acoustically transparent adhesive material 6. The acoustic window material is of a type that provides an efficient coupling and propagation of the acoustic energy from the transducer into the region of interest. The following acoustic window 7 materials may be suitable for CMUT based arrays: polybudatiene, polyether block amide (PEBAX), polydimethylsiloxane (PDMS). The optional layer of the adhesive material that fixes the patch 14 at the specified place on a body can be replaced by a strap on the back side of the support 9 (not shown). For both cases care may be taken that there is no air cavities in between the transducers and body. In ultrasound therapy/diagnostic most of the times a layer of ultrasound gel is applied in between the transducers and body. For this embodiment the strap can be applied throughout the patch or the adhesive layer can be deposited at the edges of the patch such that it does not interfere with the transmitted acoustic energy. Additionally, the patch may be coupled to a cooling circuit 25 adapted to circulate a cooling liquid around the ultrasound array. The cooling circuit can provide cooling to both: the ultrasound transducers and/or associated with them electronic circuitry; and to a body surface in contact with the patch. In the present embodiment, the cooling circuit is schematically shown to be located in between the CMUT array and the region of interest, namely on top of the optional adhesive material 6. The CMUTs array can be coupled to the transducer controller 18 via electrical interconnects 10, which may be implemented within the support 9 at an opposite to the transmission surface side of the transducers. The support 9 can be made of the flexible and/or stretchable material. Alternatively, the CMUT array and support 9 can be manufactured in a single semiconductor process flow using, for example, a flex-to-rigid technology (B. Mimoun, V. Henneken, R. Dekker, "Flex-to-Rigid (F2R): a Novel Ultra-Flexible Technology for Smart Invasive Medical Instruments", Mat. Res. Soc. Symp. Proc., San Francisco, USA, 2010). In the embodiment of FIG. 1a the interconnects 10 are bundled in a cable 11 coupling the transducers array to the transducer controller 18. In this embodiment, the controller 18 is illustrated as a separate unit. It shall be also understood by the person skilled in the art that the transducer controller 18 can also be fully integrated into the application specific circuitry embedded in the support 9 of the patch 14. The patch may comprise tracking markers 5, used in electromagnetic tracking for example, in order to track the position of the patch 14 in relation to the region of interest 12.

Figure 2:
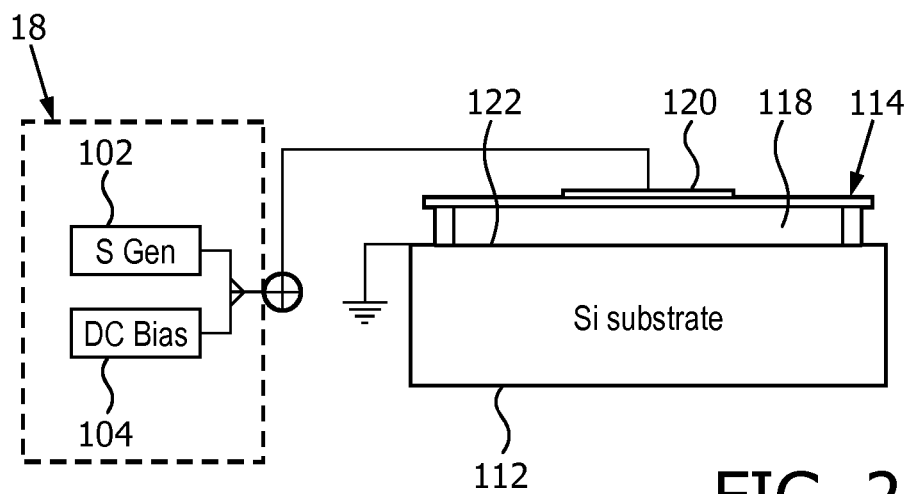
FIG. 2 illustrates a CMUT cell controlled by a DC bias voltage and driven by an r.f. drive signal.

FIG. 2 shows a CMUT cell with a membrane or diaphragm 114 suspended above a silicon substrate 112 with a gap or cavity 118 therebetween. A top electrode 120 is located on the diaphragm 114 and moves with the diaphragm and a bottom electrode is located on the floor of the cell on the upper surface of the substrate 112 in this example. Other realizations of the electrode 120 design can be considered, such as electrode 120 may be embedded in the membrane 114 or it may be deposited on the membrane 114 as an additional layer. In this example, the bottom electrode 122 is circularly configured and embedded in the substrate layer 112. In addition, the membrane layer 114 is fixed relative to the top face of the substrate layer 112 and configured and dimensioned so as to define a spherical or cylindrical gap or cavity 118 between the membrane layer 114 and the substrate layer 112.

The bottom electrode 122 is typically insulated on its cavity-facing surface with an additional layer (not shown). A preferred insulating layer is an oxide-nitride oxide (ONO) dielectric layer or so called high-k dielectric layer formed above the substrate electrode 122 and below the membrane electrode 120. The disclosed components may be fabricated from CMOS compatible materials, e.g., Al, Ti, nitrides (e.g., silicon nitride), oxides (various grades), tetra ethyl oxysilane (TEOS), poly-silicon and the like. In a CMOS fabrication, for example, the oxide and nitride layers may be formed by chemical vapor deposition or atomic layer deposition and the metallization (electrode) layer put down by a sputtering process. Suitable CMOS processes are LPCVD and PECVD, the latter having a relatively low operating temperature of less than 400° C. Exemplary techniques for producing the disclosed gap or cavity 118 involve defining the cavity in an initial portion of the membrane layer 114 before adding a top face of the membrane layer 114. Other fabrication details may be found in U.S. Pat. No. 6,328,697 (Fraser). In the exemplary embodiment depicted in FIG. 2, the diameter of the cylindrical gap or cavity 118 is larger than the diameter of the circularly configured electrode plate 122. Electrode 120 may have the same outer diameter as the circularly configured electrode plate 122, although such conformance is not required. Thus, in an exemplary implementation of the present invention, the membrane electrode 120 is fixed relative to the top face of the membrane layer 114 so as to align with the electrode plate 122 below. The electrodes of the CMUT provide the capacitive plates of the device and the gap or cavity 118 is the dielectric between the plates of the capacitor. When the diaphragm vibrates, the changing dimension of the dielectric gap or cavity between the plates provides a changing capacitance which is sensed as the response of the CMUT to a received acoustic echo. The spacing between the electrodes is controlled by applying a DC bias voltage 104 to the electrodes with a DC bias circuit. For the acoustic wave transmission the electrodes 120, 122 are driven by a signal generator 102 (S Gen) whose a.c. signal causes the diaphragm to vibrate and transmit an acoustic signal. The DC bias voltage can be analogized to a carrier wave with the a.c. signal modulating the carrier in the transmission of the acoustic signal.

The transducer controller 18 comprise the signal generator 102 and the DC bias voltage, which provides a possibility of varying the operation frequency of the CMUTs in the array. The transducer controller means 18 via the signal generator 102 can also permit varying frequency, amplitude and a pulse shape (sinus, for example) of the a.c. signal. The intensity of the transmitted acoustic signal can be adjusted by the CMUT driving scheme. For example, the transducer controller can drive the CMUT cell with the continuous sinus wave a.c. signal. Alternatively, the transducer controller drives the CMUT with the given waveform for a specified number of cycles, called a burst. The transducer controller means 18 may control the amount of time that elapses between bursts with the internal timer. Burst mode allows increasing the intensity of the transmitted acoustic wave compared to the continuous sinus waveform drive.

In accordance with the principles of the present invention the CMUT cell of the array can be operated in one of the following modes: a conventional mode and a collapsed mode.

During the conventional mode of operation the DC bias voltage 104 applied to the electrodes 120 and 122 is kept below a threshold value. This threshold value may dependent on the exact design of the CMUT cell and is defined as the DC bias voltage below which the membrane does not get stuck (contact) to the cell floor by VanderWaals force during the vibration. Thus, when the bias is set below the threshold value the membrane vibrates freely above the cell floor during operation of the CMUT cell.

The conventional mode of operation can be characterized as the mode with lower frequencies of ultrasound wave, in comparison with the collapsed mode defined below. In the conventional mode the center frequency of the CMUT cell scales inversly proportional to the cell diameter.

Figure 3A:
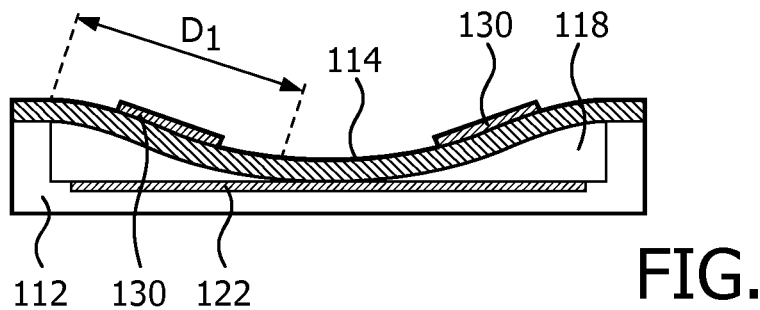
FIGS. 3a-3d illustrate the principles of collapsed mode CMUT operation applied in an implementation of the present invention.
Figure 3B:
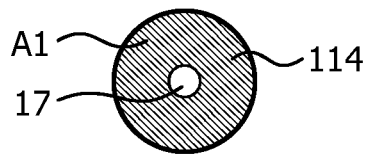

During the collapsed mode the DC bias voltage is operated at the values above the threshold. According to the present invention the CMUT cell is set by the DC bias voltage to a pre-collapsed state in which the membrane 114 is in contact with the floor of the cavity 118 as shown in FIG. 3a. This is accomplished by applying a DC bias voltage to the bottom electrode 122 and the membrane electrode(indiated by reference sign 130 in FIG. 3). In the illustrated collapsed mode implementation the membrane electrode 130 is formed as a ring electrode. Other implementations may use a continuous disk electrode as the membrane electrode, which advantageously provides the pull-down force for collapse at the center of the membrane as well as peripherally. When the membrane 114 is biased to its collapsed state as shown in FIGS. 3a and 3b, the center area of the membrane is in contact with the floor of the cavity 118. As such, the center of the membrane 114 does not move during operation of the CMUT. Rather, it is the peripheral area of the membrane 114 which moves, that which is above the remaining open void of the cavity 118 and below the ring electrode. By forming the membrane electrode 130 as a ring, the charge of the upper plate of the capacitance of the device is located above the area of the CMUT which exhibits the motion and capacitive variation when the CMUT is operating as a transducer. Thus, the coupling coefficient of the CMUT transducer is improved.

As has been indicated the membrane 114 may be brought to its collapsed state in contact with the center of the floor of the gap or cavity 118 by applying a DC bias voltage above the threshold value. This threshold value is a function of the cell diameter, the gap or cavity between the membrane and the cavity floor, and the membrane materials and thickness. As the voltage is increased, the capacitance of the CMUT cell is monitored with a capacitance meter. A sudden change in the capacitance indicates that the membrane has collapsed to the floor of the cavity. The membrane can be biased downward until it just touches the floor of the cavity as indicated in FIG. 3a, or can be biased further downward as shown in FIG. 3b to increase collapse beyond that of minimal contact, such as the area of the membrane that is collapsed to the cell floor increases.

Figure 3C:
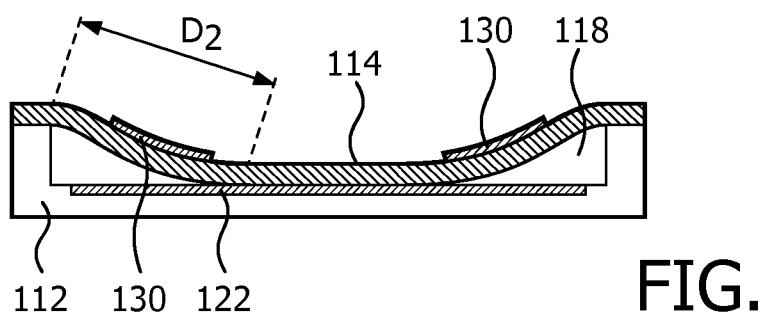

In accordance with the principles of the present invention, the frequency response of a collapsed mode CMUT is varied by adjusting the DC bias voltage 104 applied to the CMUT electrodes after collapse. As a result, the resonance frequency of the CMUT cell increases as higher DC bias is applied to the electrodes. The principles behind this phenomenon are illustrated in FIGS. 3a-3d. The cross-sectional views of FIGS. 3a and 3c illustrate this one dimensionally by the distances $D_1$ and $D_2$ between the outer support of the membrane 114 and the point where the membrane begins to touch the floor of the cavity 118 in each illustration. It can be seen that the distance $D_1$ is a relatively long distance in FIG. 3a when a relatively low bias voltage is applied after collapse, and the distance $D_2$ in FIG. 3c is a much shorter distance when a higher bias voltage is applied. These distances can be analogized to long and short strings which are held by the ends and then plucked. The long, relaxed string will vibrate at a much lower frequency when plucked than will the shorter, tighter string. Analogously, the resonant frequency of the CMUT cell in FIG. 3a will be lower than the resonant frequency of the CMUT cell in FIG. 3c which is subject to the higher DC pulldown bias voltage.

Figure 3D:
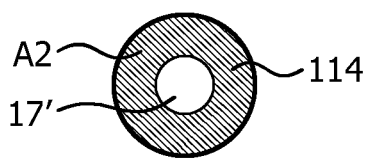

The phenomenon can also be appreciated from the two dimensional illustrations of FIGS. 3b and 3d, as it is in actuality a function of the effective operating area of the CMUT membrane. When the membrane 114 just touches the floor of the CMUT cell as shown in FIG. 3a, the effective vibrating area $A_1$ of the non-contacting (free vibrating) portion of the cell membrane 114 is large as shown in FIG. 3b. The small hole in the center 17 represents the center contact region of the membrane. The large area membrane will vibrate at a relatively low frequency. This area 17 is an area of the membrane 114, which is collapsed to the floor of the CMUT cell. But when the membrane is pulled into deeper collapse by a higher bias voltage as in FIG. 3c, the greater central contact area 17' results in a lesser free vibrating area $A_2$ as shown in FIG. 3d. This lesser area $A_2$ will vibrate at a higher frequency than the larger $A_1$ area. Thus, as the DC bias voltage is decreased the frequency response of the collapsed CMUT cell decreases, and when the DC bias voltage increases the frequency response of the collapsed CMUT cell increases.

Figure 4:
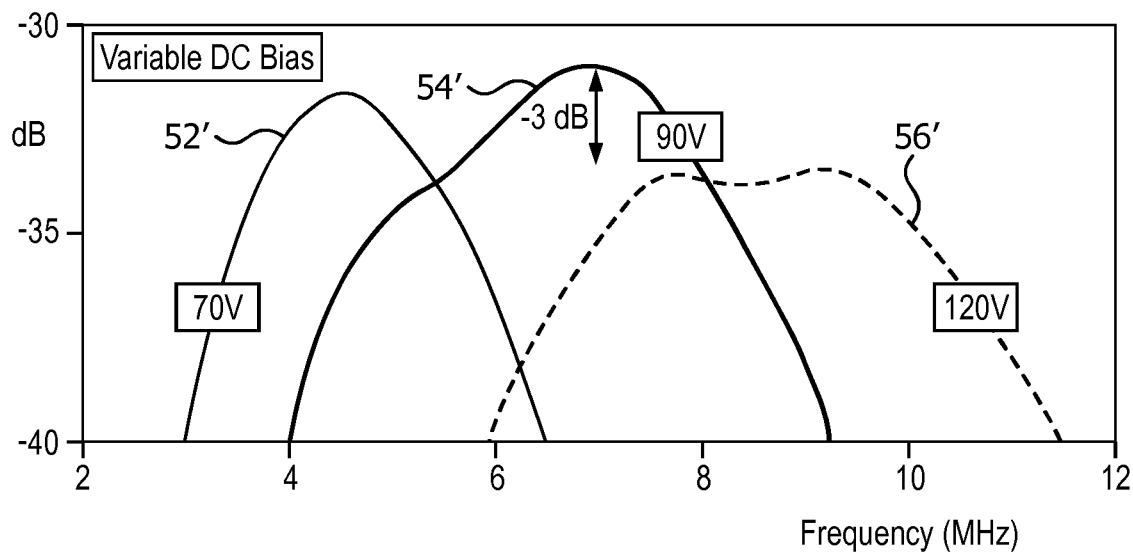
FIG. 4 illustrates the frequency response of a collapsed mode CMUT transducer with a DC bias voltage varied.

FIG. 4 illustrates how variation of the DC bias voltage of a collapsed CMUT can optimize the transducer for a particular desired frequency of operation. The figure illustrates a frequency response curve 54' for a CMUT transducer with a DC bias of 90 volts being operated in the collapsed mode, which has a nominal center frequency of around 7 MHz. When the transducer cell is operated with signals at 7 MHz it is seen that the response curve of signals around 7 MHz exhibits good sensitivity, as it is operating in the center of the transducers' passband. Changing the voltage bias shifts the passband of the operation frequencies, optimizing the frequency response of the given CMUT cell. As illustrated in FIG. 4 a DC bias of 70 volts can be used for low band operation (around 4 MHz), 90 volts can be used for mid-band operation (around 7 MHz), and 120 volts is used for high band (around 9 MHz) operation in this example, the desired passbands 52', 54' and 56' are in the center of the shifted resonant transducer passband in each case.

Figure 5:
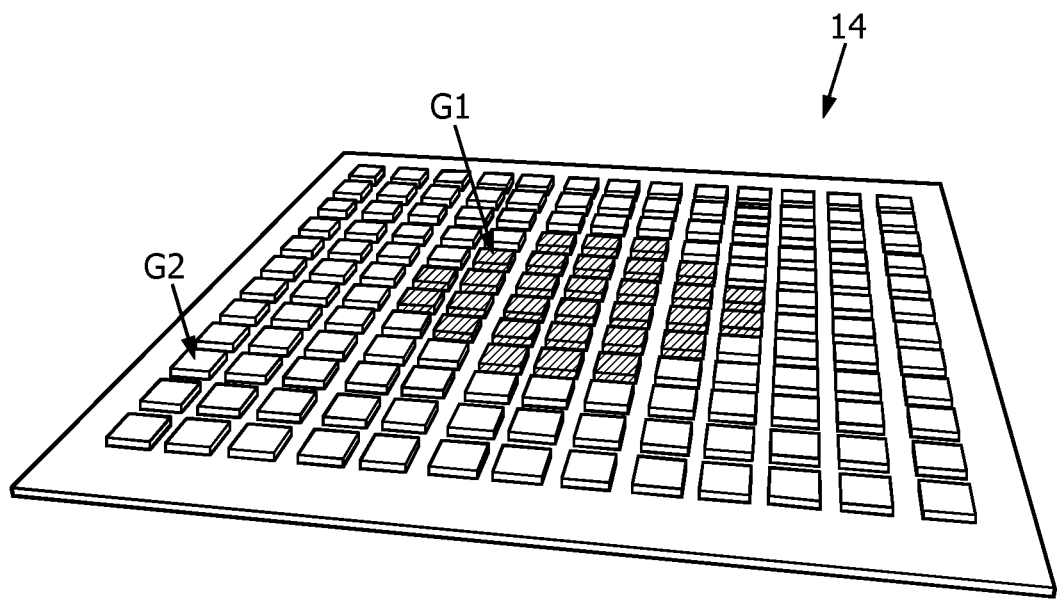
FIG. 5 illustrates the ultrasound patch of the CMUT array, comprising two concentric groups of the transducers operating at two different frequencies.

FIG. 5 illustrates the patch, wherein the transducer controller means 18 activate two groups of the transducers: G1 and G2 by applying a separate DC bias voltage and a.c f. signal values to each group. In present embodiment the groups of the transducers form concentric pattern in array. It shall be understood that more than two groups can be activated. A gradual reduction of frequency of the activated groups forming the concentric shaped patterns allows compensating for the frequency dependent acoustic wave attenuation. The innermost pattern can be formed by the group (in this example, the first group G1), which is activated to have the closest (shortest) average distance to the region of interest and to operate at a maximum frequency in a selected frequency range. The selected range (within the variable frequency range of the array) may input by the user via a user control panel 38 (see FIG. 6. The outmost pattern can be formed by the group (in this example, the second group G2), which is activated to have the farthest (largest) average distance to the region of interest and to operate at a minimum frequency in the selected frequency range. Due to the decrease in the attenuation length of the ultrasound wave in the body with increased wave frequency, this embodiment provides an improved homogeneity in acoustic wave intensity transmitted to the region of interest. This permits transmitting two groups of the ultrasound signals into the region of interest having different frequencies and spatially separated from each other. In addition, the transducer controller means 18 can control an amount or density of the CMUT transducers activated in the pattern within one group, which gives an additional control over an intensity of the transmitted HIFU signal. It shall be also noted that the acoustic power (intensity equals to power distributed per area) of the transmitted ultrasound wave can be also controlled by the DC bias voltage applied to the cell. The amount of groups of the activated transducers can depend on the configuration (shape, dimensions, etc.) of the region of interest.

Figure 7A:
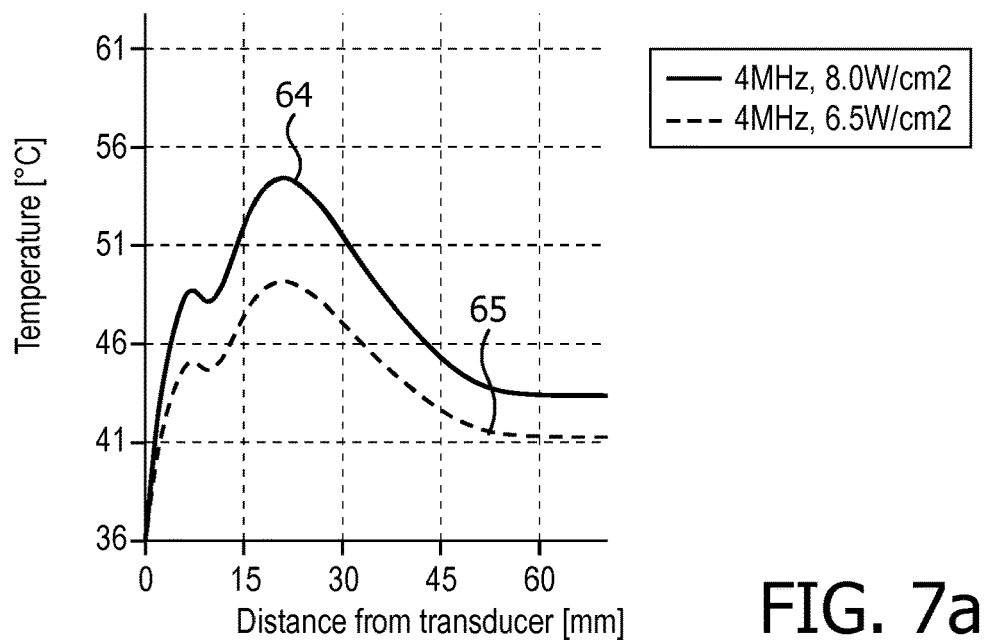
FIG. 7a-c illustrates the modeled tissue temperature profiles in lateral and depth directions caused by the ultrasound signal having variable intensity.
Figure 7B:
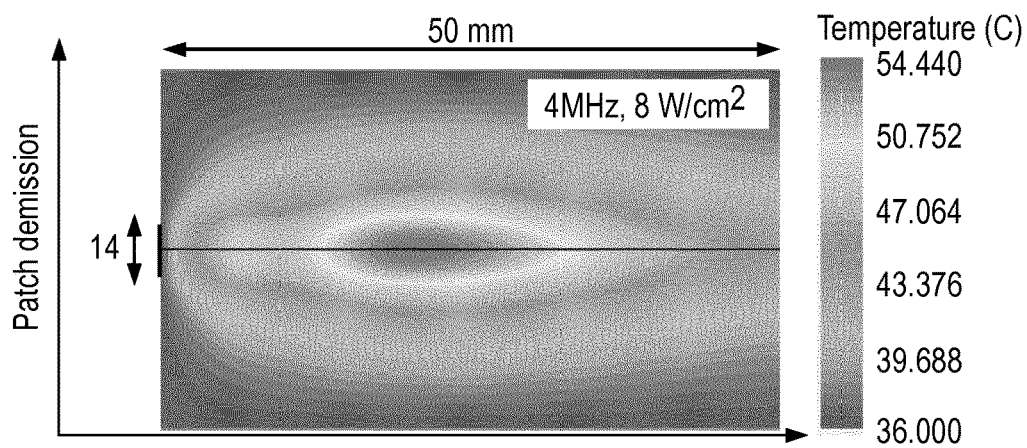
Figure 7C:
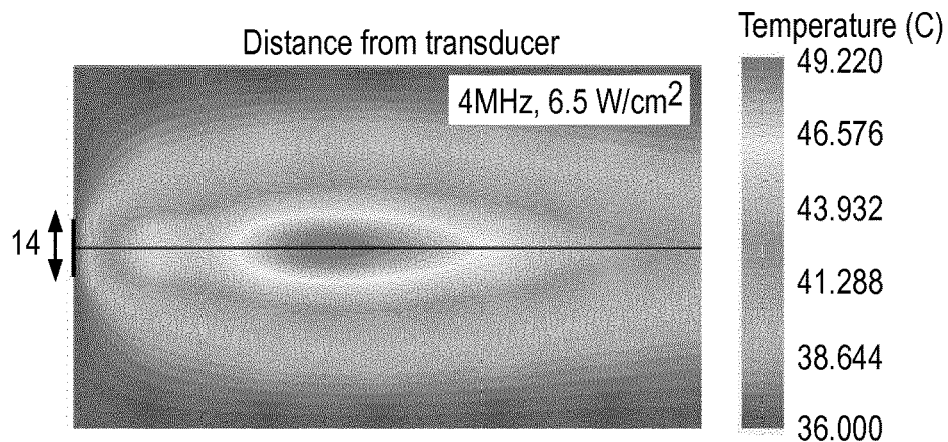
Figure 8A:
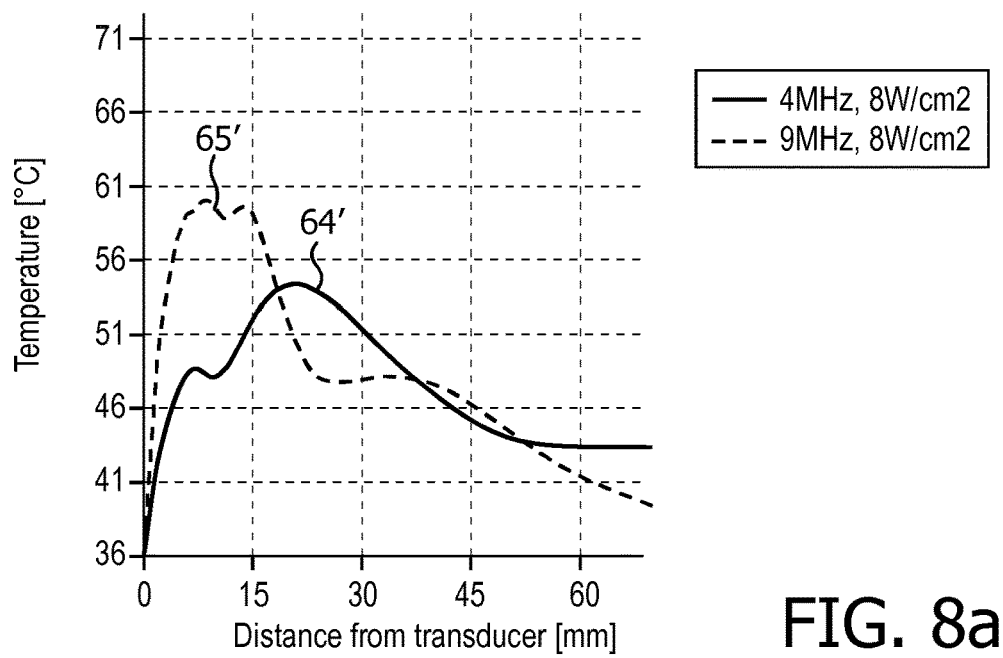
FIG. 8a-c illustrates the modeled tissue temperature profiles in lateral and depth directions caused by the ultrasound signal having variable frequency.
Figure 8B:
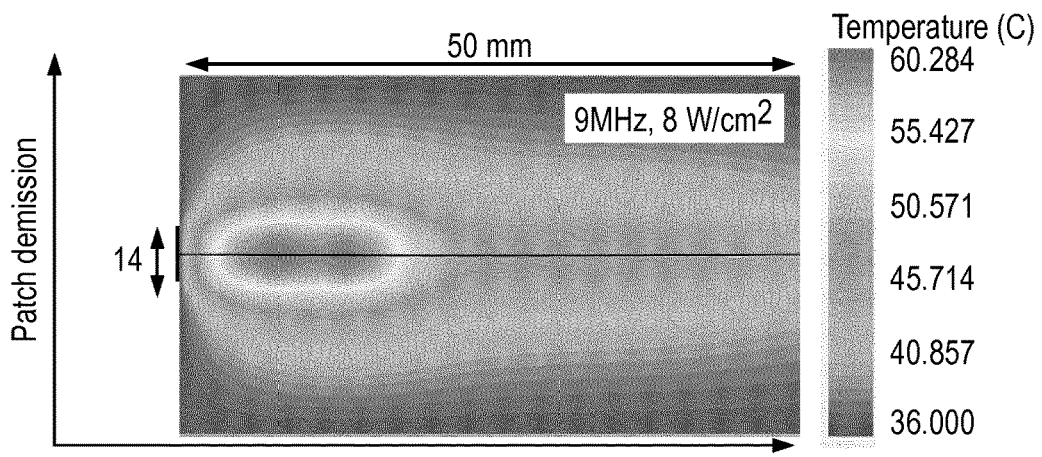
Figure 8C:
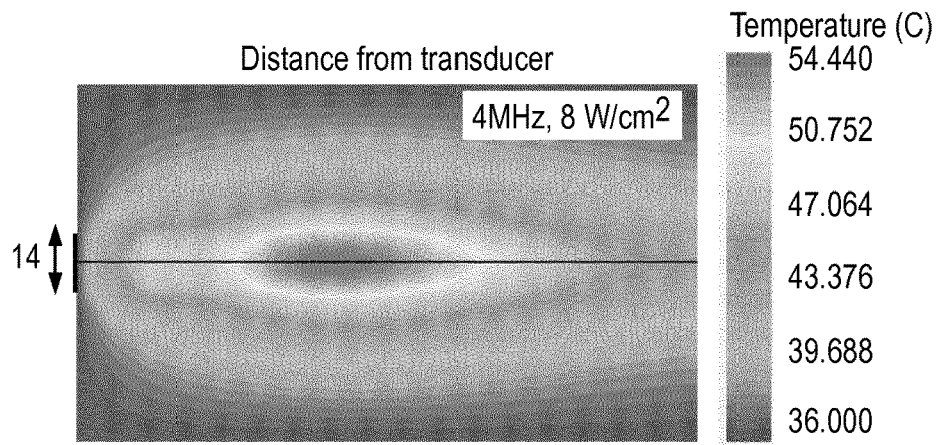

FIGS. 7 and 8 illustrate of the effect of the groups' frequency and intensity variation on the temperature depth profile (distance from the transducer) in the region of interest. The profiles are simulated with STAR-CCM+ from CD-Adapco. The model includes a Pennes-like formulation (for bioheat transfer), i.e., thermal source is due to absorption of the propagating ultrasound waves, thermal "leak" is due to blood perfusion (taken uniform over the tissue), and soft tissue is described by its thermodynamic properties (such as density, thermal conductivity, heat capacity). For this particular case following assumptions are used: the region of interest comprises a soft tissue, the patch comprises an array of 4 by 5 mm with CMUT cells having diameters of 120 micrometers. In all simulations the soft tissue is described by a simplified model with the same properties for the whole tissue volume. The acoustic properties were kept constant in time with acoustic impedance in the range of 1.5-1.65 MRayls and absorption in the range 0 (lossless media)-0.5 dB/cm/MHz. The thermal model is based on a generalized bioheat equation, wherein the tissue's heat conductivity was taken 0.4-0.5 W/mK and heat capacity 2500-3500 J/kg/K. The blood perfusion term was included on basis of an effective heat source (leak), corresponding to the perfusion rate between 0-0.5 mL/g/min.

The profile 64 in FIG. 7a corresponds to the case, wherein all CMUTs are operating at the same frequency of 4 MHz the intensity of the transmitted by the array ultrasound signal is 8 W/cm$^2$. As can be seen the main maximum in the temperature profile 64 is at 55 centigrade and located at an average distance of 20 mm away from the transducers. An intensity reduction of the ultrasound signal down to 6.5 W/cm$^2$ causes the temperature profile 65 with temperature maximum value at about 49 centigrade and at the same average distance. Since the frequency of the signal is still the same there is no apparent change in the temperature depth penetration for the HIFU signal.

FIG. 7b illustrates temperature distribution of the profile 64 in two dimensions. The horizontal axis corresponds to the distance from transducer in millimeters, wherein the entire profile 64 expands from zero to 50 mm, and the vertical axis corresponds to the largest dimension of the patch 14, wherein a scale of 5 mm with an arrow is indicated.

The temperature is indicated with different contrasts and changes from 36 up to 54.4 centigrade (the temperature scale is to the right from the figure), wherein the maximum in the temperature profile is located at an average distance of 20 mm. FIG. 7c illustrates temperature distribution of the profile 65 in the same dimensions. As can be seen, the temperature distribution is quite symmetric around the axis perpendicular to the patch surface and the profile maximum is located in the same region for the same frequency of the ultrasound treatment. Application of the lower ultrasound intensity lowers the induced increase in the temperature, such that the maximum temperature at the profile maximum reaches 49.2 centigrade.

FIG. 8a illustrates the simulated temperature profiles for the same tissue as in the previous example, wherein the frequency of the ultrasound signal is varied. The profile 65' represents a penetration of the ultrasound signal having 9 MHz frequency and 8 W/cm$^2$ intensity into the region of interest. As can be seen the main temperature maximum is at 60 centigrade and located at the average distance of 7 mm from the transducer array. Lowering the frequency of the ultrasound signal down to 4 MHz (keeping intensity at the same level) increases its penetration depth as seen from the profile 64' and causes the maximum temperature of around 54 centigrade at the average distance of about 20 mm.

FIG. 8b illustrates temperature distribution of the profile 65' in two dimensions. The horizontal axis corresponds to the distance from transducer in millimeters, wherein the entire profile 65' expands from zero to 50 mm, and the vertical axis corresponds to the largest dimension of the patch 14, wherein a scale of 5 mm with an arrow is indicated.

The temperature is indicated with different contrasts (the temperature scale is to the right from the figure) and changes from 36 up to 60 centigrade, wherein the maximum in the temperature profile is located at an average distance of 7 mm. FIG. 7c illustrates temperature distribution of the profile 64' in the same dimensions. As can be seen, the temperature distribution for both frequencies is quite symmetric around the axis perpendicular to the patch surface. In the lower frequency case the profile maximum is located farther from the transducer at about 20 mm distance. The induced increase in the temperature also changes with frequency, wherein the maximum profile temperature reaches 54 centigrade. Thus, with frequency variation of the ultrasound we can adjust both the penetration distance and the temperature of the treatment.

Figure 9A:
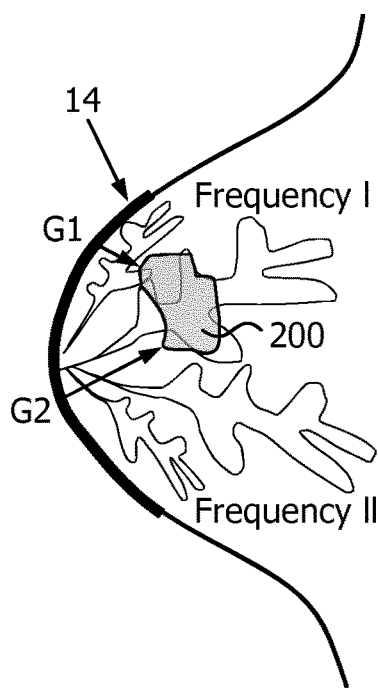
FIG. 9a illustrates a body conformable patch applied to a breast in the region of interest.
Figure 9B:
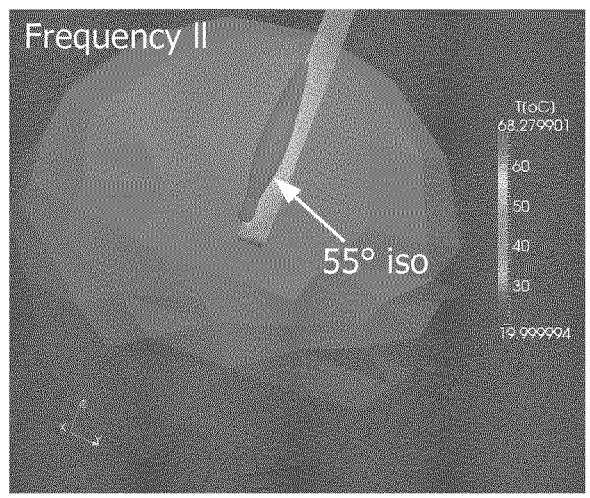
FIG. 9b-c illustrate a modeled temperature profiles in the breast caused by the high intensity ultrasound signals simultaneously transmitted by two groups of the transducers operating at relatively lower and higher frequencies correspondingly.
Figure 9C:
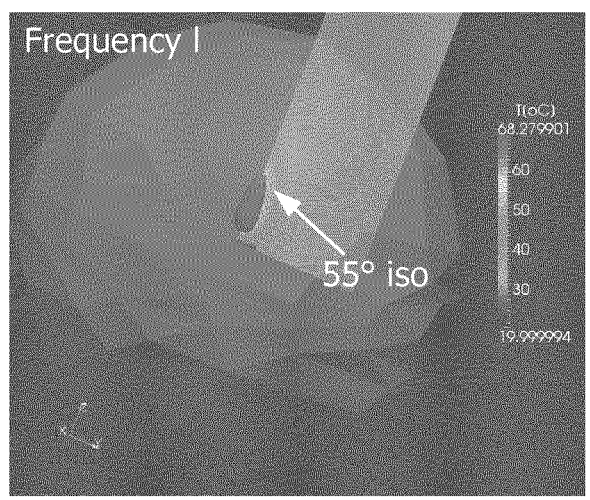

FIG. 9 shows a specific implementation of the present invention for the hyperthermia treatment of a breast tumor 200 with the ultrasound treatment patch 14 of 3 by 3 millimeters in size (dimensions) with CMUT cells having diameters of 120 micrometers. In this example, the patch has a CMUT array arranged on the flexible support, this type of flexible CMUT arrays can be manufactured using the known flexible-to-rigid semiconductor techniques. Preferably, the patch 14 also comprises an adhesive layer material 6 (or a strap) as shown in FIG. b providing a full conformity of the patch with the breast shape as shown in FIG. 9a. The transducer controller 18 of FIG. 1a activates two groups of the CMUTs, wherein a first group G1 has the average distance to the tumor shorter than the average distance between the tumor and a second group G2. Both groups simultaneously transmit signal at two different frequencies, wherein the first group's frequency is higher than the second group's frequency: the first group's frequency I is 5 MHz and the second group's frequency II is 10 MHz. The patch was assumed to be at 20 centigrade (which in practice can be achieved by coupling the patch 14 to the cooling circuit 25) and the intensity of the ultrasound signal was 15 W/cm$^2$. FIG. 9b shows the 3D simulation of the temperature distribution caused by the heating with the ultrasound signal transmitted by the second group and FIG. 9c shows the 3D simulation of the temperature distribution caused by the heating with the ultrasound signal transmitted by the first group. The combined effect of the ultrasound signals transmitted by both groups is a localized area of the increased temperature corresponding to the dimensions of the tumor located in the region of interest.

Figure 6:
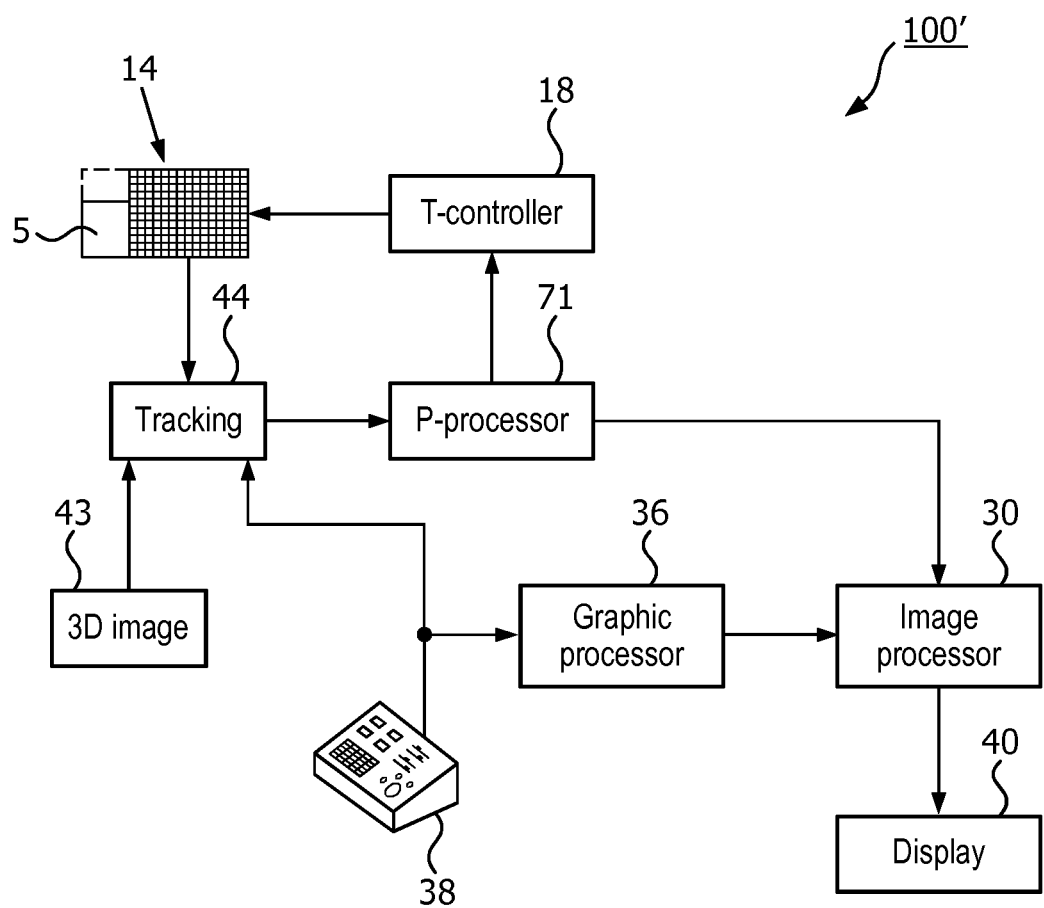
FIG. 6 illustrates a block-diagram of the ultrasound systems in accordance with another embodiment of the present invention.

FIG. 6 illustrates a block-diagram of the ultrasound system 100' in accordance with another embodiment of the present invention. This embodiment provides a patient specific ultrasound or ablation treatment, which can be tuned for each specific case (tumor). The tracking markers 5, which are located on the patch 14, supply a data of the patch's location to tracking means 44. The tracking means 44 are adapted to register the patch's position in relation to the region of interest into a 3D medical image 43 of the region of interest. Further, the registered 3D image of the region of interest provided by the tracking means is being processed at a pattern processor 71. The pattern processor identifies the dimensions of the tumor and its projection under different angles onto the patch (average distance from the array transducers to the tumor). Based on this processed information the pattern processor calculates the amount of groups, their patterns, frequencies and intensities at which the 2D array will be activated. This information is being supplied to the transducer controller 18, which activates the predefined groups in the array.

The tracking means 44 may receive input from a user control panel 38, such as the point in the anatomy of an image where the tumor is located. A graphics processor 36 is coupled to the input of the control panel 38 and can generate graphic overlays for display with the medical images. These graphic overlays can contain standard identifying information such as patient name, date and time of the image, imaging parameters, and the like. For these purposes the graphics processor receives input from the control panel 38, such as a typed patient name. The user interface can also be coupled to the transducer controller 18 (not shown) to control the treatment procedure and provide the ability of aborting the treatment in case of need. The graphic overlays generated by graphic processor 36 are combined with the defined patterns of the groups in the patch and the registered medical images by an image processor 30. The image processor outputs the combined images and patient's specific information onto a display 40. The image processor can also store or upload to a cloud server all data related to the given hyperthermia treatment.

The 3D medical image 43 can be an image either obtained before the treatment or a real-time image acquired by the known medical imaging techniques, such as X-ray, MRI and ultrasound. The MRI or ultrasound diagnostic techniques can also provide a real-time measurement of the temperature of the region of interest. In the case of real-time guided ultrasound therapy the user can monitor the temperature distribution in the region of interest in real-time and the pattern processor may perform a real-time processing update for the groups and their characteristics (pattern, frequency, intensity) activated via the transducer controller 18. The temperature monitoring provides an improved therapy control.

The ultrasound system for an ultrasound therapy of the present invention can also include an application specific circuitry adapted to perform acoustic beam focusing which can improve the delivered thermal dose (amount of the acoustic energy delivered to the region of interest) to the region of interest by generating an arbitrary shaped acoustic beam patterns. The circuitry can also perform a function of either partial or full beamforming of the transmitted and received ultrasound signals. Combined with a standard ultrasound image processing means, such an ultrasound system may be used for both applications: hyperthermia treatment and ultrasound imaging.

While preferred ultrasound intensity ranges like 4 to 10 W/cm$^2$, 4 to 50 W/cm$^2$ may be determined by the desired treatment procedure, such as ablation or hypertermia, the application of the focusing means in the patch 14 may reduce the required ultrasound intensity for the treatment down to 100 mW/cm$^2$. Therefore, the intensity range of the ultrasound signals which are simultaneously transmitted by the patch may vary from 100 m W/cm$^2$ to 4 W/cm$^2$ and 100 m W/cm$^2$ to 52 W/cm$^2$.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

The invention claimed is:

1. An ultrasound system for an ultrasound therapy of a region of interest comprising:
   a patch comprising a two-dimensional array of a plurality of ultrasound transducers arranged on a flexible support, wherein the two-dimensional array comprises:
   a first group of the plurality of ultrasound transducers comprising a first pattern and adapted to transmit ultrasound signals with a first frequency in a collapsed mode responsive to a first DC bias voltage; and
   a second group of the plurality of ultrasound transducers comprising a second pattern and adapted to transmit the ultrasound signals with a different, second frequency in the collapsed mode responsive to a different, second DC bias voltage;
   a transducer controller adapted to operate the two-dimensional array by activating the first group and the second group to transmit the ultrasound signals into the region of interest for therapeutic heating of the region of interest;
   a tracking processor adapted to register the patch into a medical image of the region of interest obtained by an imaging device, wherein the imaging device is different than the patch; and
   a pattern processor coupled to the transducer controller, wherein the pattern processor is adapted to process the medical image to define the first pattern, the second pattern, the first frequency, and the second frequency, wherein the defining is based on:
   dimensions of the region of interest; and
   a first distance and a second distance from the region of interest to the first group and the second group, respectively,
   wherein the transducer controller is further adapted to provide:
   the first DC bias voltage to the first group such that, at the first distance, the ultrasound signals transmitted with the first frequency in the collapsed mode provide a first temperature for the therapeutic heating in the region of interest and
   the second DC bias voltage to the second group such that, at the second distance, the ultrasound signals transmitted with the second frequency in the collapsed mode provide a second temperature for the therapeutic heating in the region of interest.

2. The ultrasound system according to claim 1, wherein the second frequency is smaller than the first frequency.

3. The ultrasound system according to claim 1,
   wherein the first pattern and the second pattern form concentric shapes,
   wherein the first group comprises an innermost pattern and the first frequency is a maximum frequency of the first group and the second group, and
   wherein the second group comprises an outermost pattern and the second frequency is a minimum frequency of the first group and the second group.

4. The ultrasound system according to claim 1, wherein the plurality of the ultrasound transducers is adapted to operate in a variable frequency range, wherein the variable frequency range expands from 500 kHz up to 10 MHz.

5. The ultrasound system according to claim 1, wherein the transducer controller is adapted to activate the first group to transmit the ultrasound signals with a first intensity and the second group to transmit the ultrasound signals with a different, second intensity.

6. The ultrasound system according to claim 5, wherein the plurality of the ultrasound transducers is adapted to operate in a variable intensity range, wherein the variable intensity range comprises one of 4 to 10 W/cm$^2$, 4 to 50 W/cm$^2$, 100 mW/cm$^2$ to 4 W/cm$^2$, or 100 mW/cm$^2$ to 52 W/cm$^2$.

7. The ultrasound system according to claim 1, wherein the patch further comprises an adhesive layer material conformable with a patient's body.

8. The ultrasound system according to claim 1,
   wherein a first intensity of the ultrasound signals transmitted by the first group is predefined by the first distance, and
   wherein a second intensity of the ultrasound signals transmitted by the second group is predefined by the second distance.

9. The ultrasound system according to claim 1, wherein the patch further comprises an integrated circuitry coupled to the plurality of ultrasound transducers and adapted to provide at least partial beamforming of the ultrasound signals.

10. A method of an ultrasound therapy of a region of interest comprising:
    providing a patch comprising a two-dimensional array of a plurality of ultrasonic transducers arranged on a flexible support, wherein the two-dimensional array comprises:
    a first group of the plurality of ultrasound transducers comprising a first pattern and adapted to transmit ultrasound signals with a first frequency in a collapsed mode responsive to a first DC bias voltage; and
    a second group of the plurality of ultrasound transducers comprising a second pattern and adapted to transmit the ultrasound signals with a different, second frequency in the collapsed mode responsive to a different, second DC bias voltage;
    providing a transducer controller adapted to operate the two-dimensional array by activating the first group and the second group to transmit the ultrasound signals into the region of interest for therapeutic heating of the region of interest;
    tracking to register the patch into a medical image of the region of interest obtained by an imaging device, wherein the imaging device is different than the patch;
    processing the medical image to define the first pattern, the second pattern, the first frequency, and the second frequency, wherein the defining is based on:
    dimensions of the region of interest; and
    a first distance and a second distance from the region of interest to the first group and the second group, respectively; and
    controlling, based on the pattern and the frequency of each group, a first of the at least two groups to provide a first therapeutic heating profile at a first position in the region of interest and a second of the at least two groups to provide a second therapeutic heating profile at a second position in the region of interest providing, with the transducer controller:
    the first DC bias voltage to the first group such that, at the first distance, the ultrasound signals transmitted with the first frequency in the collapsed mode provide a first temperature for the therapeutic heating in the region of interest; and the second DC bias voltage to the second group such that, at the second distance, the ultrasound signals transmitted with the second frequency in the collapsed mode provide a second temperature for the therapeutic heating in the region of interest.

11. The method according to claim 10 further comprising the first frequency or the second frequency during the therapy.

12. The method according to claim 10 further comprising defining the first intensity of the ultrasound signals transmitted by the first group based on the first distance and the second intensity of the ultrasound signals transmitted by the second group based on the second distance.

13. The ultrasound system according to claim 1, wherein the patch comprises an entire area formed by the flexible support, wherein the entire area is continuous.

14. The ultrasound system according to claim 1, wherein the patch comprises a cooling circuit adapted to circulate a cooling liquid around the two-dimensional array and maintain flexibility of the flexible support to conform to a body surface, wherein the cooling circuit is located between the two-dimensional array and the region of interest.

15. The ultrasound system according to claim 1, wherein the transducer controller is further adapted to at least one of vary the first frequency by adjusting the first DC bias voltage or vary the second frequency by adjusting the second DC bias voltage.

16. The ultrasound system according to claim 1, wherein the transducer controller is configured to control:
the first group to provide a first therapeutic heating profile in the region of interest based on the first pattern and the first frequency; and
the second group to provide a second therapeutic heating profile in the region of interest based on the second pattern and the second frequency,
wherein the first therapeutic heating profile and second therapeutic heating profile are three-dimensional.

17. The ultrasound system according to claim 1, wherein the first group and the second group are adapted to simultaneously transmit the ultrasound signals with the first frequency and the ultrasound signals with the second frequency, respectively.

18. The ultrasound system according to claim 1, wherein the first distance comprises an average distance between the region of interest and the first group and the second distance comprises an average distance between the region of interest and the second group.

* * * * *